May 31, 1966 E. S. BOERNER Plant Pat. 2,637
CHRYSANTHEMUM PLANT
Filed May 19, 1965
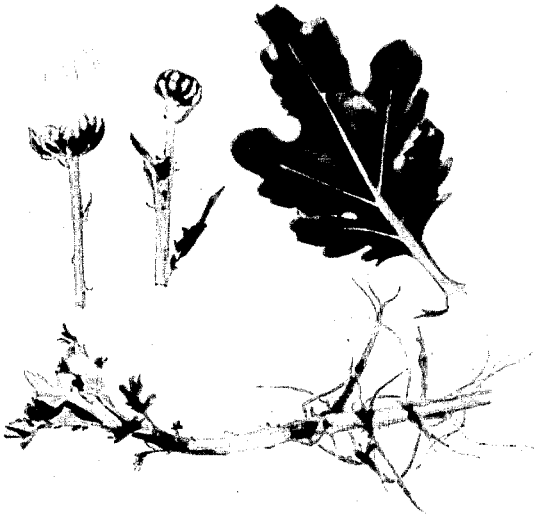
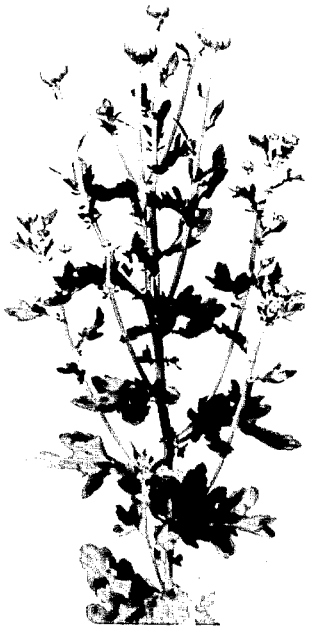
Inventor.
E. S. Boerner
By: Robb & Robb
Attorneys.

United States Patent Office

Plant Pat. 2,637
Patented May 31, 1966

2,637
CHRYSANTHEMUM PLANT

Eugene S. Boerner, Newark, N.Y., assignor to Jackson & Perkins Company, Newark, N.Y., a corporation of New York Filed May 19, 1965, Ser. No. 457,233
1 Claim. (Cl. Plt.—77)

This invention relates to a new and distinct variety of chrysanthemum plant of the decorative class, which was originated by me by crossing the chrysanthemum variety known as "Golden Scepter" (unpatented) with the chrysanthemum variety known as "Golden Cockatoo" (Plant Patent No. 1,638).

The primary objective of this breeding was to produce a new chrysanthemum variety having an early blooming habit corresponding to the parent variety "Golden Cuckatoo," combined with a large flower size corresponding to the parent variety "Golden Scepter." This objective was fully achieved along with other desirable improvements, as evidenced by the following unique combination of characteristics which are outstanding in the new variety and which distinguish it from its parents, as well as from all other varieties of which I am aware:

(1) A vigorous and bushy plant habit;
(2) An early blooming habit;
(3) A large flower size, with many petals per bloom;
(4) A reflexed flower petal habit; and
(5) A distinctive and attractive general color tonality of the flowers, said flowers being White, with the lower half of the petals very lightly overcast with Citron Yellow.

Asexual reproduction of the new variety by both top cuttings and underground runners, as performed at Newark, N.Y., shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen stem which is depicted in black and white for the purpose of illustrating the form and habit of growth of the plant.

The following is a detailed description of the new variety, with color terminology in accordance with Ridgway's Color Standards and Nomenclature.

Parentage: Seedling.
*Seed parent.*—"Golden Scepter."
*Pollen parent.*—"Golden Cockatoo."
Classification: Decorative.
Growth: From 20–22 inches high.

Location where observations made: Outdoors at Newark, N.Y., in the early morning during first part of the month of October.
Cold resistance: Hardy in northern New York State.
Blooming period: From mid-September until frost.

*Flower*

Bud:
*Color.*—When petals first divide—Ivory Yellow, Plate 30, lightly overcast with Pinkish Buff, Plate 29. When petals begin to unfurl—Marguerite Yellow, Plate 30, very lightly overcast with Straw Yellow, Plate 16. When half-blown: Inside—White, Plate 53, with lower half of petal very lightly overcast with Pinard Yellow, Plate 4; outside—White, Plate 53, very lightly overcast with Sea-Foam Yellow, Plate 31, in the lower half of the petal.
*Peduncle.*—Color—Chromium Green, Plate 32. Strength—strong.

Bloom:
*Size*—From 5½ inches to 6 inches in diameter.
*Stem.*—Strong.
*Form.*—Decorative, with petals reflexed.
*Petalage.*—Long, with many petals to flower.
*Color.*—Center of flower—Amber Yellow, Plate 16. Outer petals—White, Plate 53. Base of petals—Deep Sea-Foam Green, Plate 31. Inside of petals—White, Plate 53, with lower half of petal very lightly overcast with Citron Yellow, Plate 16. Reverse of petals—White, Plate 53.
*Petals.*—Texture—thick. Form—oval.
*Fragrance.*—Characteristic chrysanthemum.

*Plant*

Form: Bushy.
Growth: Very free.
Foliage:
*Size.*—Medium.
*Quantity.*—Normal.
*Color.*—Upper side—Cress Green, Plate 31. Reverse side—Light Cress Green, Plate 31.
*Texture.*—Leathery.

I claim:

A new and distinct variety of chrysanthemum plant of the decorative class, substantially as herein shown and described, characterized particularly as to novelty by the unique combination of a vigorous and bush plant habit, an early blooming habit, a large flower size, with many petals per bloom, a reflexed flower petal habit, and a distinctive and attractive general color tonality of the flowers, said flowers being White, with the lower half of the petals very lightly overcast with Citron Yellow.

No references cited.

ABRAHAM G. STONE, *Primary Examiner.*